(12) United States Patent
Churchill et al.

(10) Patent No.: US 8,447,625 B2
(45) Date of Patent: May 21, 2013

(54) SYSTEMS AND METHODS FOR TECHNICAL SUPPORT SESSIONS

(75) Inventors: Todd W. Churchill, Kansas City, MO (US); Daniel P. Cowan, Kansas City, MO (US); Chuck P. Tenney, Kansas City, MO (US)

(73) Assignee: Cerner Innovation, Inc., Lenexa, KS (US)

( * ) Notice: Subject to any disclaimer, the term of this patent is extended or adjusted under 35 U.S.C. 154(b) by 1608 days.

(21) Appl. No.: 11/260,301

(22) Filed: Oct. 27, 2005

(65) Prior Publication Data

US 2007/0095354 A1 May 3, 2007

(51) Int. Cl.
*G06Q 50/00* (2006.01)

(52) U.S. Cl.
USPC .............................. 705/2; 705/7.14; 705/304

(58) Field of Classification Search .................. 705/2–4, 705/7.14, 304
See application file for complete search history.

(56) References Cited

U.S. PATENT DOCUMENTS

| 6,477,531 | B1 * | 11/2002 | Sullivan et al. ................. 707/10 |
| 7,313,228 | B1 * | 12/2007 | Sorice et al. ............... 379/88.17 |
| 2004/0139156 | A1 * | 7/2004 | Matthews et al. ............ 709/204 |

OTHER PUBLICATIONS

Hornbill systems: Waveney district council selects hornbill's supportworks for IT helpdesk; local authority chooses high functionality IT helpdesk system to streamline support processes and meet new government standards for IT service management. (Dec. 6, 2005). M2 Presswire. Retrieved from http://search.proquest.com/docview/445734810?accountid=147.*

* cited by examiner

*Primary Examiner* — Mark Holcomb
(74) *Attorney, Agent, or Firm* — Shook, Hardy & Bacon L.L.P.

(57) ABSTRACT

Systems and methods for providing technical support sessions to aid clinicians and other end users employing clinical applications are provided. In accordance with one method in a clinical computing environment for requesting a technical support session between a client device and at least one support device, a command to request the technical support session is received. Clinical context information associated with the client device is accessed. A request for the technical support session is communicated. In addition, the clinical context information associated with the client device is communicated.

13 Claims, 19 Drawing Sheets

TASK EDIT VIEW OPTIONS CURRENT ADD HELP

DOE, JANE   AGE: 5 YEARS   SEX: FEMALE   LOCATION: GIRAFFE; 10; B ** NO KNOWN ALERGY
                DOB: 2/12/2000   MRN: BWMC 000-635   FIN NUMBER: 003489   INPATIENT [10/8/2004 5:59]

AS OF: 9:31 AM   CUSTOM

| REFERENCE | PT SCHED | ORDERS | FORM BROWSER |
| PATIENT INFO | LAST 48 HOURS | VITAL SIGNS | LAB | RAD | REPORTS | INTERACTIVE VIEW | GRAPHS | ACQUIRED DATA | MAR | FLUIDS | PT SUMMARY | MED HX | SCRIPT WRITER |

POWERORDERS  — 510

512

VIEW

- ORDERS FOR SIGNATURE
- PLANS
  - DOCUMENT IN PLAN
- ORDERS PROFILE
  - ☑ PROBLEMS
  - ☑ PATIENT STATUS
  - ☑ ALLERGIES
  - ☑ VITAL SIGNS
  - ☑ ACTIVITY
  - ☑ DIET
  - ☑ NURSING ORDERS
  - ☑ IV SOLUTIONS
  - ☑ MEDICATIONS
  - ☑ LABORATORY
  - ☑ DIAGNOSTIC TESTS
  - ☑ CONSULTS
  - ☑ ANCILLARY SERVICES
  - ☑ ORDERSETS
  - ☑ SURGICAL PROCEDURE

ORDERS FOR SIGNATURE  ROWS SELECTED (0)

| ☐ PROBLEMS | |
| ☐ FEVER | 5/23/2005 |
| ☐ SKIN INTEGRITY IMPAIRMENT RISK | 1/1/2005 |
| ☐ EXOPHAGEAL ATRESIA | 2/1/2005 |
| PATIENT STATUS | |
| ☐ ALLERGIES | |
| ※ NO KNOWN ALLERGIES | |
| VITAL SIGNS | |
| ACTIVITY | |
| DIET | |
| NURSING ORDERS | |
| IV SOLUTIONS | |
| MEDICATIONS | |
| LABORATORY | |
| DIAGNOSTIC TESTS | |
| CONSULTS | |
| ANCILLARY SERVICES | |
| ORDERSETS | |
| SURGICAL PRICEDURE | |

RELATED RESULTS   ◄ DETAILS

*(Screenshot of electronic medical record application showing patient DOE, JANE with a screensharing chat dialog:)*

KATE REPRESENT: HOW CAN I HELP YOU TODAY?
JOE PHYSICIAN: I PLACED AN ORDER FOR 250 MG OF PENICILLIN, BUT CAN NOT FIND IT ON MY PATIENT'S CHART.
KATE REPRESENT: DR. PHYSICIAN, IT MAY BE EASIER FOR BOTH OF US IF I WERE ABLE TO VIEW YOUR SCREEN. IS THAT ALRIGHT WITH YOU?
JOE PHYSICIAN: SURE THAT WOULD BE GREAT.
KATE REPRESENT: IN A FEW SECONDS YOU WILL SEE A PROMPT REQUESTING PERMISSION TO SEE AND SHARE YOUR SCREEN. PLEASE SELECT "OK" TO THIS REQUEST.

SYSTEMS AND METHODS FOR TECHNICAL SUPPORT SESSIONS

CROSS-REFERENCE TO RELATED APPLICATIONS

Not applicable

STATEMENT REGARDING FEDERALLY SPONSORED RESEARCH OR DEVELOPMENT

Not applicable

TECHNICAL FIELD

The present invention relates to the field of computer software. More specifically, the present invention also relates to technical support sessions (e.g., real-time sessions) for assisting clinicians.

BACKGROUND OF THE INVENTION

Information technology has become the "silent partner" for clinicians as they practice medicine. A number of clinical applications are available that aid clinicians in many facets of their practice, including business management and patient care. One example of such a clinical application is the Cerner Millennium® application available from Cerner Corporation of North Kansas City, Mo. These clinical applications often allow clinicians to effectively manage vast amounts of healthcare related information. However, if clinicians have difficulties with these clinical applications, the information may not be readily available 24 hours a day, seven days a week, potentially causing the healthcare process to become dangerously slow and more prone to errors. As a result, clinicians actively engaged in critical healthcare functions need a support system that is ready at an instant, so that the medical process can continue unabated.

Clinicians often require immediate answers to their questions in order to provide high quality patient care. Clinicians are highly mobile and typically are not in one place long enough to receive a response to their request for assistance if the response is not immediate. Currently, when clinicians need assistance with clinical applications, the clinicians may contact a help desk to request support. For example, a clinician who has difficulty accessing a portion of a patient's record within a particular clinical application may send an email to the help desk detailing the problem. The help desk may receive the email and then either attempt to call the clinician or reply to the email. However, there is often a lag between the clinician's email and the help desk's response. The clinician may no longer be available if the help desk attempts to call the clinician, or the clinician may no longer have access to the clinical application if the clinician is at a new location. An email response would allow the clinician to review the response at a convenient time, but if the information is needed immediately, such a response may be untimely and therefore ineffective. Moreover, if the initial email response is inadequate to address the issue faced by a clinician, resolution of that issue may require a time-consuming back and forth process between the clinician and the help desk.

Alternatively, the clinician may place a phone call request for assistance to the help desk. However, the help desk may not be readily available to adequately assist the clinician. For example, the particular issue faced by the clinician may require a person at the help desk who has the technical capacity to address the issue. This may involve an escalation in which the clinician is forwarded to various representatives at the help desk until a representative who is capable of assisting the clinician is reached. This may be a timely process that is unacceptable to the clinician.

A further drawback to current approaches to assist clinicians with clinical applications is that help desk representatives often do not have specific information that would aid the process, such as characteristics of the clinical application, characteristics of the computing environment, and information regarding the clinician requesting support, for example. Typically, a clinician can attempt to provide such information and explain the issue for which the clinician is seeking assistance. However, if the clinician does not know particular information and/or has difficulty explaining the issue, the support process will be hindered.

Accordingly, it would be desirable to provide effective technical support to clinicians using clinical applications. In addition, the ability to automatically provide support representatives with information to aid the process, such as information regarding the clinical applications, would be advantageous. It would also be helpful to automatically route clinicians to the appropriate support representative. Further, because healthcare information is typically sensitive material, it would be beneficial if HIPAA (Health Insurance Portability & Accountability Act) compliance and security was maintained during such support sessions.

SUMMARY OF THE INVENTION

Embodiments of the present invention provide systems and methods for technical support sessions to aid clinicians and other end users employing clinical applications. Accordingly, in one aspect, an exemplary embodiment of the invention is directed to a method in a clinical computing environment for requesting a technical support session between a client device and at least one support device. The method includes receiving a command to request the technical support session. The method also includes accessing clinical context information associated with the client device. The method further includes communicating a request for the technical support session. The method still further includes communicating the clinical context information associated with the client device.

In another aspect of the invention, an embodiment relates to a method in a clinical computing environment for initiating a technical support session between a client device and at least one support device. The method includes receiving a request to initiate a technical support session for a client device. The method also includes receiving clinical context information associated with the client device. The method further includes initiating a technical support session between the client device and the at least one support device.

In yet another aspect, an embodiment is directed to a method in a clinical computing environment for providing technical support to a client device. The method includes receiving clinical context information associated with a client device. The method also includes presenting the clinical context information on a support device.

In a further aspect of the invention, an embodiment is directed to a computerized system in a clinical environment for providing a technical support session between a client device and a support device. The system includes a clinical support application and a technical support application. The clinical support application is capable of requesting a technical support session between the client device and the support device. The clinical support application is also capable of accessing and communicating clinical context information associated with the client device. The technical support application is capable of receiving the clinical context information associated with the client device and presenting the clinical context information on the support device.

Still a further aspect of the invention relates to a user interface embodied on at least one computer readable medium. The user interface is for requesting a technical support session between a client device and a support device. The user interface comprises a session request display area that is configured to receive a user indication to request a technical support session, wherein upon receiving a user indication, a request for the technical support session is initiated and clinical context information associated with the client device is accessed for the technical support session.

BRIEF DESCRIPTION OF THE DRAWINGS

The present invention is described below in detail with reference to the attached drawing figures, wherein:

Figure 5B:
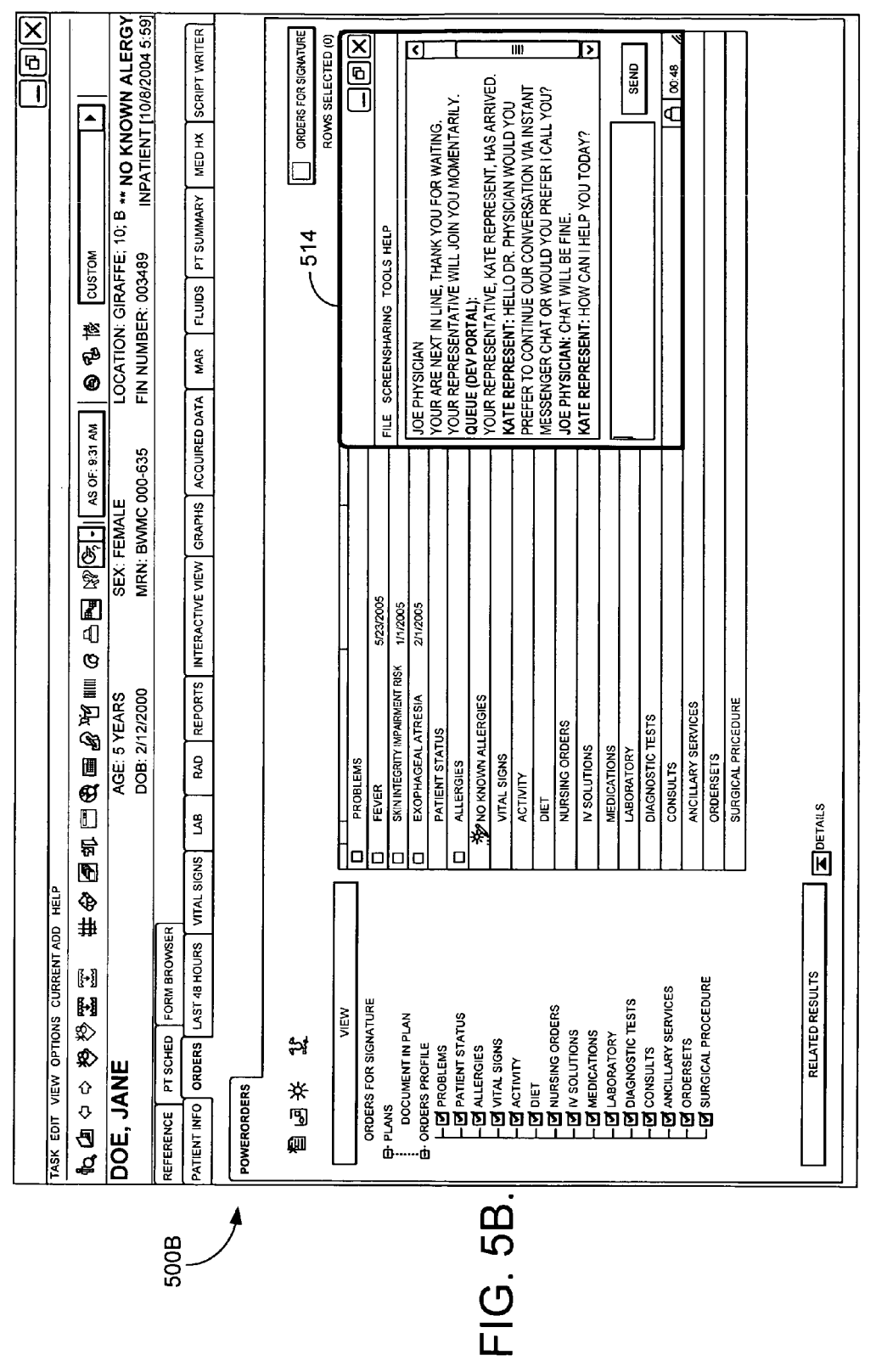
Figure 5C:
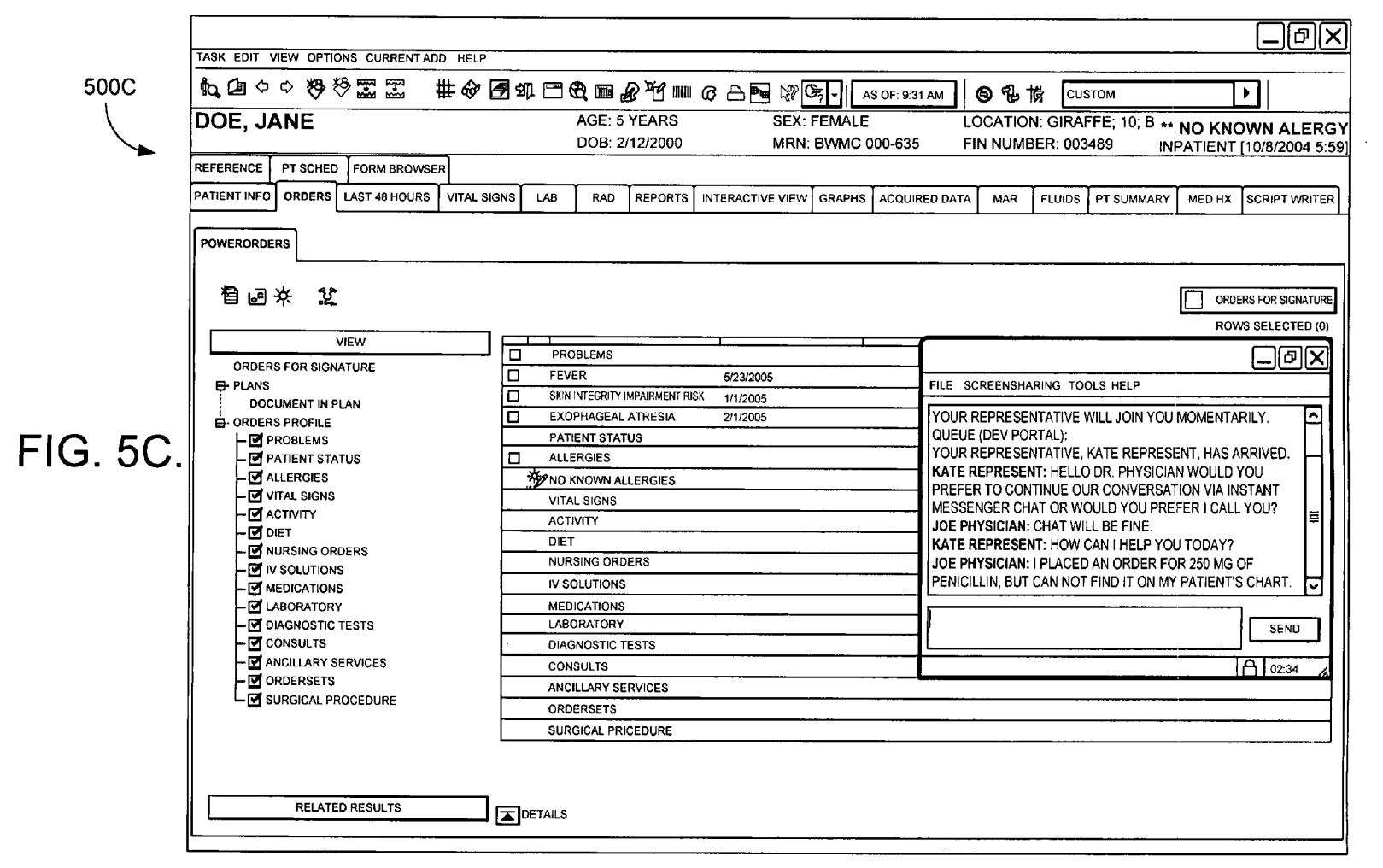
Figure 5F:
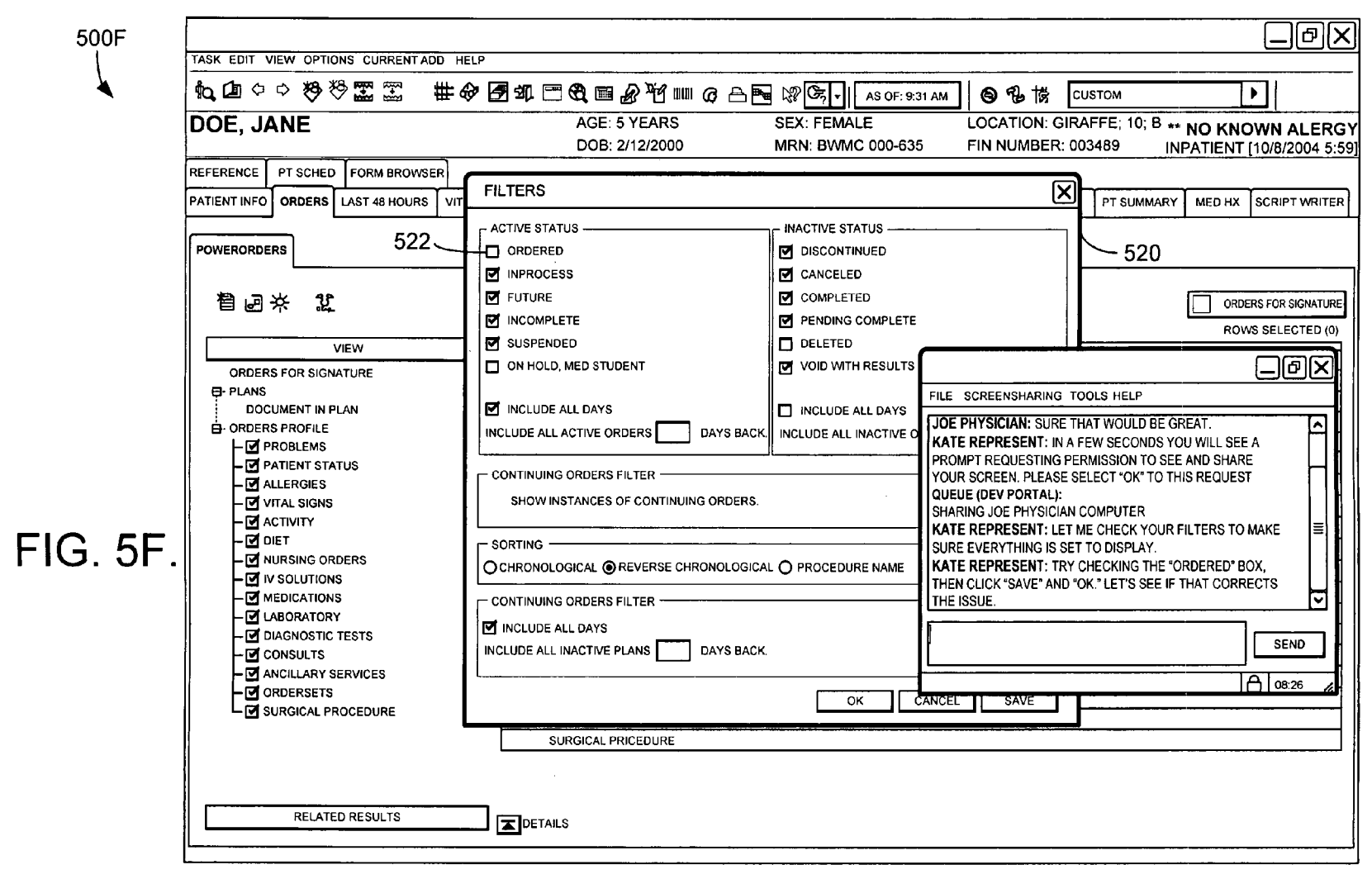
Figure 5G:
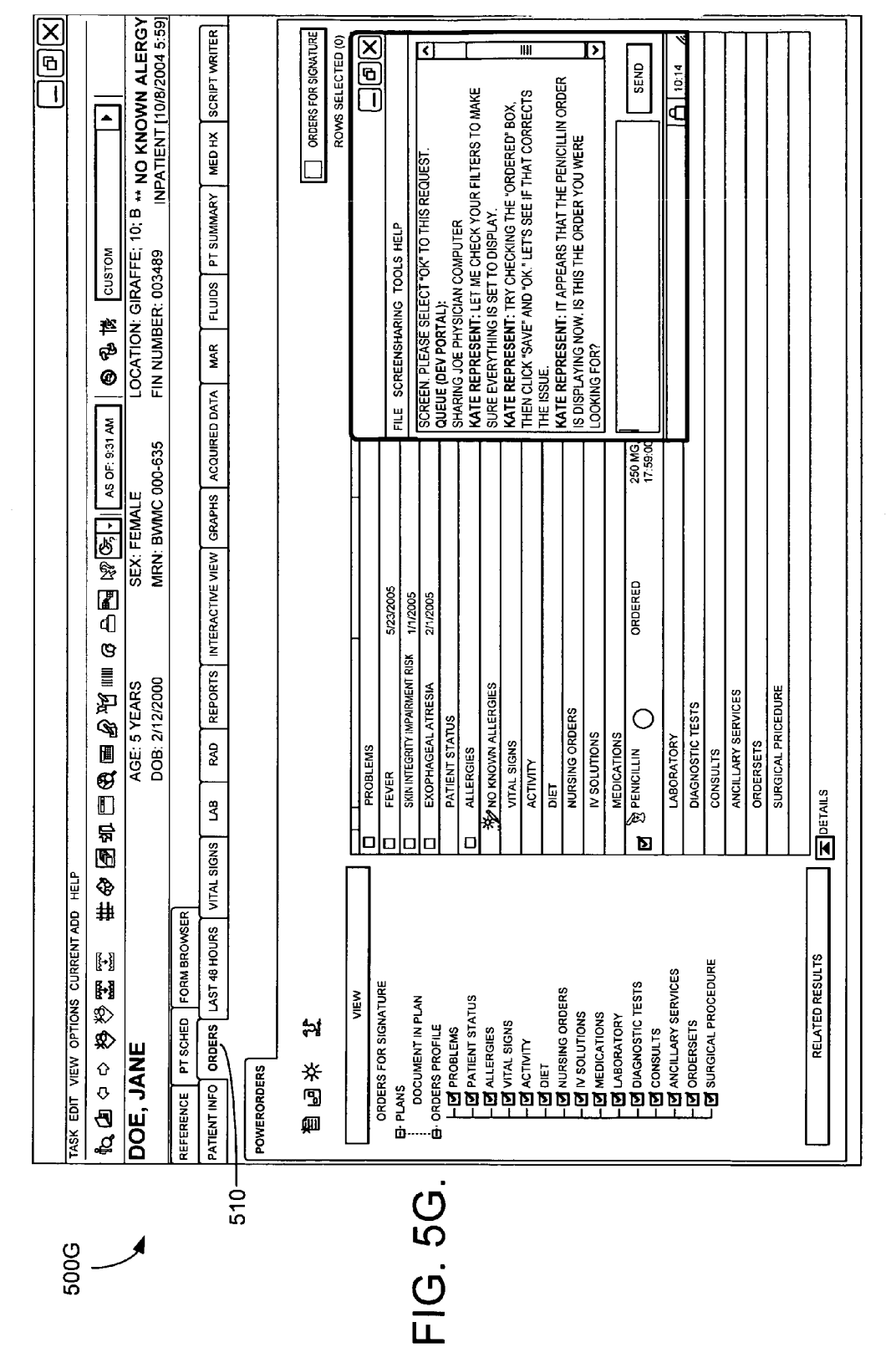
Figure 5H:
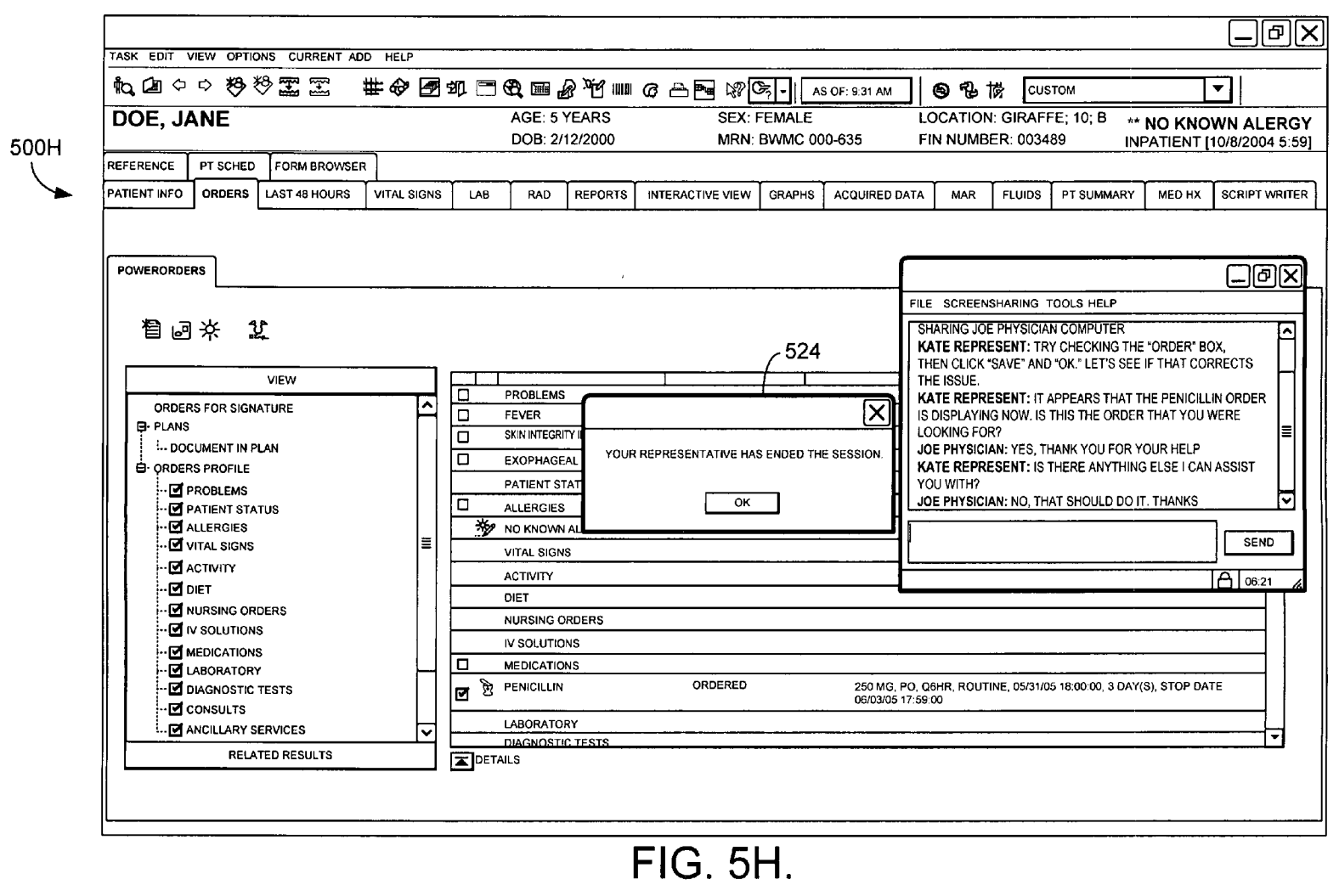

FIG. 5A through FIG. 5H are exemplary screen displays from a client device during a technical support session in a clinical environment in accordance with an embodiment of the present invention.

DETAILED DESCRIPTION OF THE INVENTION

Figure 1:
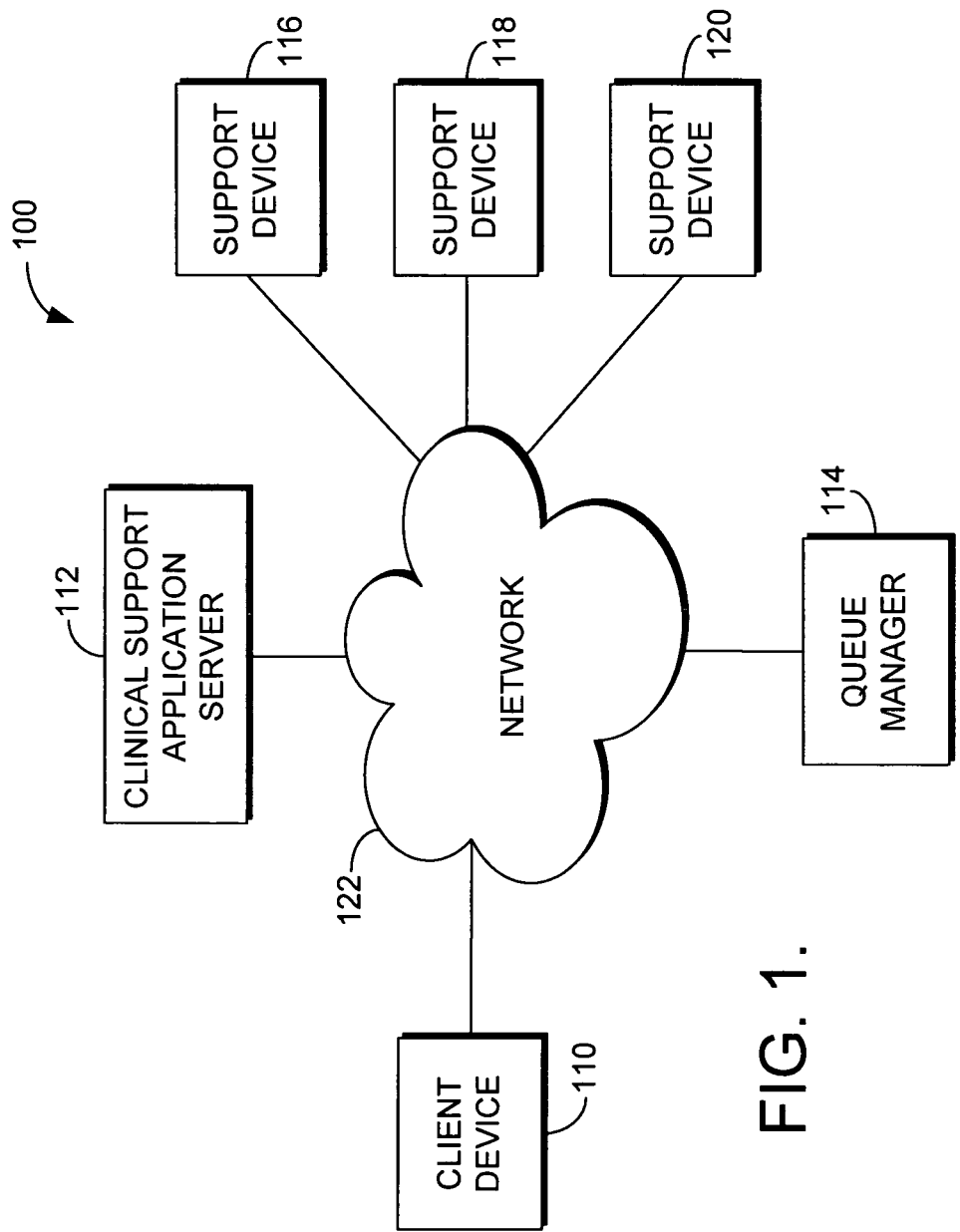
FIG. 1 is a block diagram of a computing system environment of an embodiment of the present invention.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

The present invention may be implemented in a variety of computing system environments. For example, the invention may be embodied in an application program running on one or more personal computers (PCs). This computing system environment is only one example of a suitable computing environment and is not intended to suggest any limitation as to the scope of use or functionality of the invention. The invention may also be implemented with numerous other general purpose or special purpose computing system environments or configurations. Examples of other well-known computing systems, environments, and/or configurations that may be suitable for use with the invention include, but are not limited to, server computers, hand-held or laptop devices, multiprocessor systems, microprocessor-based systems, programmable consumer electronics, network PCs, minicomputers, mainframe computers, distributed computing environments that include any of the above systems or devices, and the like.

The invention may be described in the general context of computer-executable instructions, such as program modules. Generally, program modules include routines, programs, objects, components, segments, schemas, data structures, etc. that perform particular tasks or implement particular abstract data types. The invention may also be practiced in distributed computing environments where tasks are performed by remote processing devices that are linked through a communications network. In a distributed computing environment, program modules may be located in both local and remote computer storage media including memory storage devices.

Computers typically include a variety of computer-readable media. Computer-readable media includes any media that can be accessed by a computer and includes both volatile and nonvolatile media, removable and non-removable media. By way of example, and not limitation, computer-readable media may comprise computer storage media and communications media. Computer storage media include both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD), holographic or other optical storage, magnetic cassettes, magnetic tape, magnetic disk storage or other magnetic storage devices, or any other medium which can be used to store the desired information and which can be accessed by a computer.

Communications media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communications media includes wired media such as a wired network or direct wired connection, and wireless media such as acoustic, RF, infrared, spread spectrum and other wireless media. Communications media are commonly used to upload and download information in a network environment, such as the Internet. Combinations of any of the above should also be included within the scope of computer-readable media.

The computer may operate in a networked environment using logical connections to one or more remote computers, such as a personal computer, a server, a router, a network PC, a peer device or other common network node, and typically includes many or all of the elements described above. The logical connections may include connections to a local area network (LAN), a wide area network (WAN) and/or other networks. Such networking environments are commonplace in offices, enterprise-wide computer networks, intranets and the Internet.

Computer storage mechanisms and associated media provide storage of computer-readable instructions, data structures, program modules and other data for the computer. A user may enter commands and information into the computer through input devices such as a keyboard, pointing device (commonly referred to as a mouse), trackball or touch pad. Other input devices may include a microphone, touchscreen, camera, joystick, game pad, scanner, or the like. In addition to a monitor or other type of display device, computers may also include other peripheral output devices such as speakers and printers, which may be connected through an output peripheral interface.

Although many other internal components of computers have not been discussed herein, those of ordinary skill in the art will appreciate that such components and their interconnection are well-known. Accordingly, additional details concerning the internal construction of computers need not be disclosed in connection with the present invention.

Embodiments of the present invention provide systems and methods for providing a technical support session in a clinical environment between an end user and a support representative. In some embodiments of the invention, the technical support session is a real-time session between the end user and support representative. With reference to FIG. 1, a block diagram of an exemplary embodiment of the invention is provided that illustrates a system 100 for providing clinical support to end users, such as clinicians (e.g., physician, nurses, caregivers, and the like). Among other components not shown, the system 100 may include a client device 110, a clinical support application server 112, a queue manager 114, and a number of support devices, such as support devices 116, 118, 120. Each of the components may communicate, for example, via a network 122. The network 122 may include one or more wide area networks (WANs) and/or one or more local area networks (LANs), as well as one or more public networks, such as the Internet, and/or one or more private networks. Although system 100 illustrates three support devices 116, 118, 120 and one client device 110, clinical support application server 112, and queue manager 114 communicating via the network 122, it should be understood that any number for each type of component may be included within the system 100. All such variations are within the scope of the present invention.

The client device 110 is the device at which an end user, such as a clinician, requests support. Although a clinician is often to referred herein as the end user, it should be understood that any person authorized to access a clinical application and that may require assistance may be considered the end user requesting support in accordance with embodiments of the invention. Typically, the client device 110 is also the device at which the end user requires assistance. The client device 110 may be any type of general purpose or special purpose computing device. By way of example only and not limitation, the client device 110 may be a personal computer, a handheld device, a laptop computer, a medical device, or other type of computing device.

Figure 2:
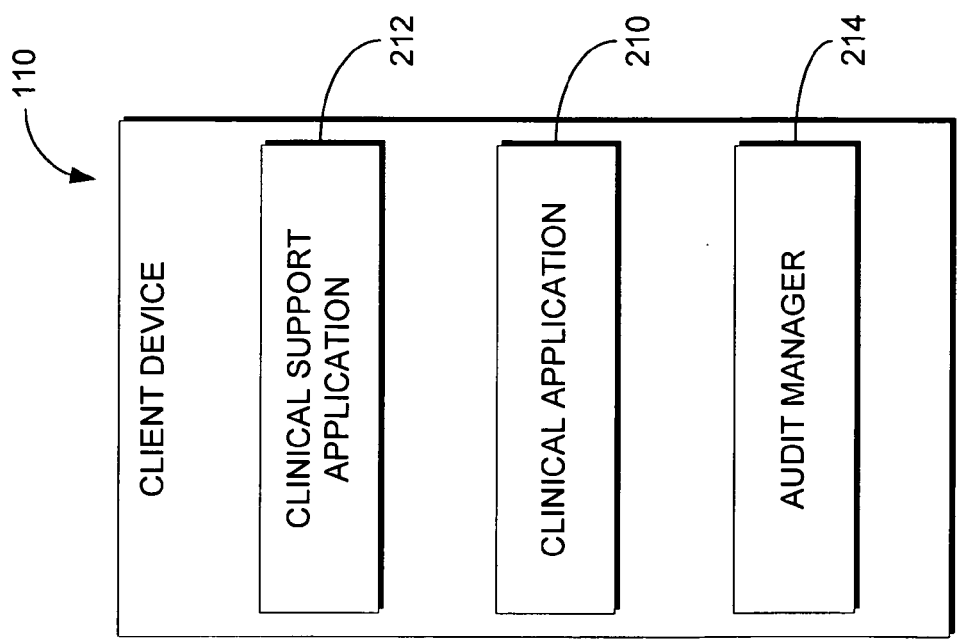
FIG. 2 is a block diagram of an exemplary client device in accordance with an embodiment of the present invention.

An exemplary client device 110 in accordance with an embodiment of the present invention is illustrated in FIG. 2. Among other components, the client device 110, or a device associated with the client device 110, may include a clinical application 210. Generally, the clinical application 210 may be any type of application directed towards healthcare management, such as, for example, the Cerner Millennium® application available from Cerner Corporation of North Kansas City, Mo. Although the client device 110 is shown with only one clinical application 210, it should be understood that multiple clinical applications may reside and be running on the client device 110 within the scope of the present invention.

The client device 110 may also include a clinical support application 212. The clinical support application 212 allows for technical support sessions to be initiated and carried out on the client device 110 in accordance with various embodiments of the present invention. In addition, the clinical support application 212 (or another component, such as a clinical support application server 112, which is shown in FIG. 1 and is discussed in further detail below) may collect clinical context information from the client device 110 and make the information available to a support representative during a support session. The clinical context information includes any data that may aid a support representative in assisting an end user during a support session. The clinical context information may include, for example, characteristics of the client device 110, characteristics of the clinical application 210, and information pertaining to the end user. By way of example only and not limitation, clinical context information may include an end user's name, an end user's location, an end user's role, an ID for the clinical application 210, the name of the clinical application 210, a current tab or location open within the clinical application 210, the location of the client device 210, software characteristics of the client device 110, and hardware characteristics of the client device 110 (e.g., memory, processing power, etc.).

In some embodiments, the clinical support application 212 may be a thick application, wherein the bulk of the processing required for initiating and carrying out a support session is performed by the clinical support application 212 residing on the client device 110. In other embodiments, the clinical support application 212 may be a thin application, wherein the bulk of the processing required for initiating and carrying out a support session may be performed by another component separate from the client device 110 (e.g., a clinical support application server 112, which is shown in FIG. 1 and discussed in further detail below).

The client device 110 may further include an audit manager 214. The audit manager 214 may collect various information from a support session, such as text, statistics, and actions taken. The information may then be accessed for auditing, HIPAA compliance, and other issues. Although the audit manager 214 is shown as a separate component residing on the client device 110, it should be noted that the audit manager 214 may be a component of the clinical support application 212 in some embodiments of the invention. In addition, the audit manager 214 may be separate from the client device 110 in other embodiments of the invention. For example, a single audit manager 214 may be provided within a hospital network to support multiple client devices. In addition, the audit manager 214 may be a component residing within a clinical support application server 214 (discussed in further detail below).

Referring again to FIG. 1, to support a thin clinical support application 212 for the client device 110, the system 100 may include a clinical support application server 112. The clinical support application server 112 then provides the bulk of the processing required to initiate and carry out a technical support session for the client device 110. For example, using a thin clinical support application 212, the client device 110 may be able to access the clinical support application server 112 via a WAN to initiate and carry out a technical support session. In another embodiment, the client device 110 and clinical support application server 112 may both be part of the same LAN, such as a computer network within a hospital. The client device 110 may then access the clinical support application server 112 within the LAN for a technical support session. In a further embodiment, the client device 110 may simply include a web browser, which may be used to communicate with the clinical support application server 112 via the Internet.

The system 100 may also include an initiation application, such as a queue manager 114, for example. The queue manager 114 serves as a gateway between the client device 110 and a support device, such as the support devices 116, 118, 120. The queue manager 114 may receive a request for a support session from the client device 110 and initiate a support session with one of the support devices 116, 118, 120. In some embodiments of the invention, the queue manager 114 may contain logic to select a particular support device for the support session based on clinical context information accessed from the client device 110.

The system 100 further includes a number of support devices, such as support devices 116, 118, 120. Each support device 116, 118, 120 represents a computing device at which a support representative may participate in a support session to assist an end user at the client device 110. As with the client device 110, the support devices 116, 118, 120 may each be any type of general purpose or special purpose computing device. By way of example only and not limitation, each of the support devices 116, 118, 120 may be a personal computer, a handheld device, a laptop computer, or other type of computing device.

Figure 3:
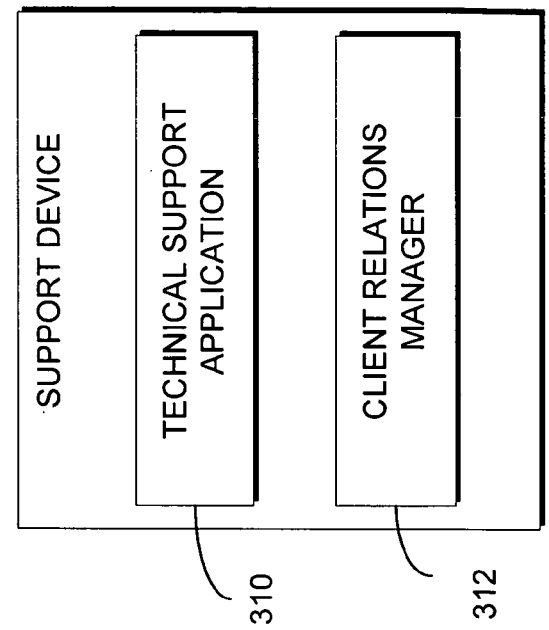
FIG. 3 is a block diagram of an exemplary support device in accordance with an embodiment of the present invention.

An exemplary support device 116 in accordance with an embodiment of the present invention is illustrated in FIG. 3. Among other components, the support device 116 may include a technical support application 310 that provides the capability to communicate with the client device 110 via a support session. In addition, the technical support application 310 may be provided clinical context information from the client device 110. The clinical context information may then be presented to a support representative operating the support device 116.

Similar to the audit manager 214 for the client device 110, the support device 116 may also include a client relations manager 312 for collecting information during support sessions for auditing and other purposes. Although the client relations manager 312 is shown as a separate component within the support device 116, the client relations manager 312 may be a component of the technical support application 310 in an embodiment of the invention. In another embodiment of the invention, the client relations manager 312 may be separate from the support device 116. For example, a single client relations manager 312 may be provided for multiple support devices, such as for the support devices 116, 118, 120 (FIG. 1). In yet a further embodiment of the present invention, a component may be provided that performs session auditing for both client devices and support devices.

Although many other internal components of the client device 110, clinical support application server 112, queue manager 114, and support devices 116, 118, 120 are not shown, those of ordinary skill in the art will appreciate that such components and their interconnection are well known. Accordingly, additional details concerning the internal construction of the client device 110, clinical support application server 112, queue manager 114, and support devices 116, 118, 120 are not further disclosed herein.

Figure 4:
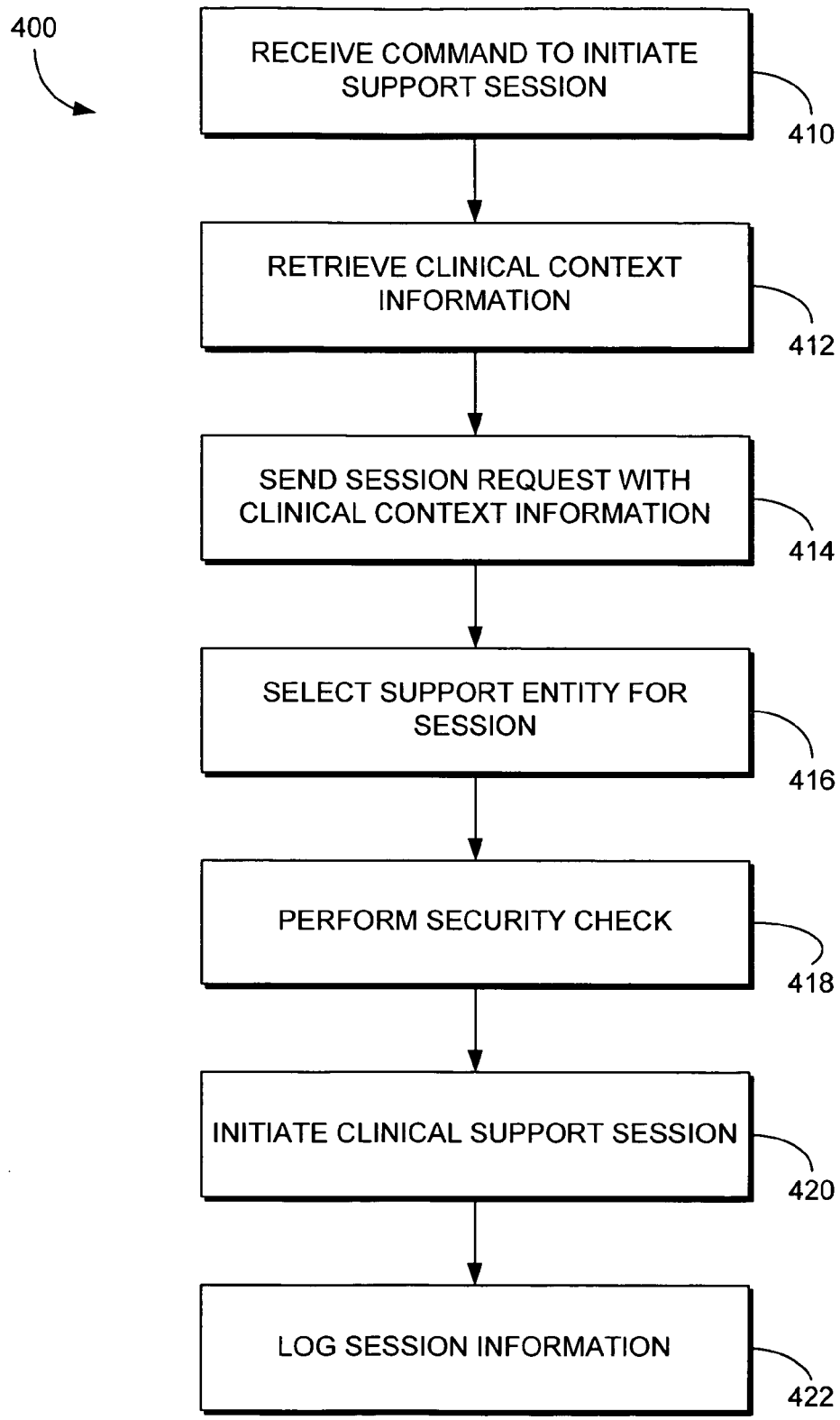
FIG. 4 is a flow diagram of a method for initiating a technical support session in a clinical environment in accordance with an embodiment of the present invention.
Figure 5E:
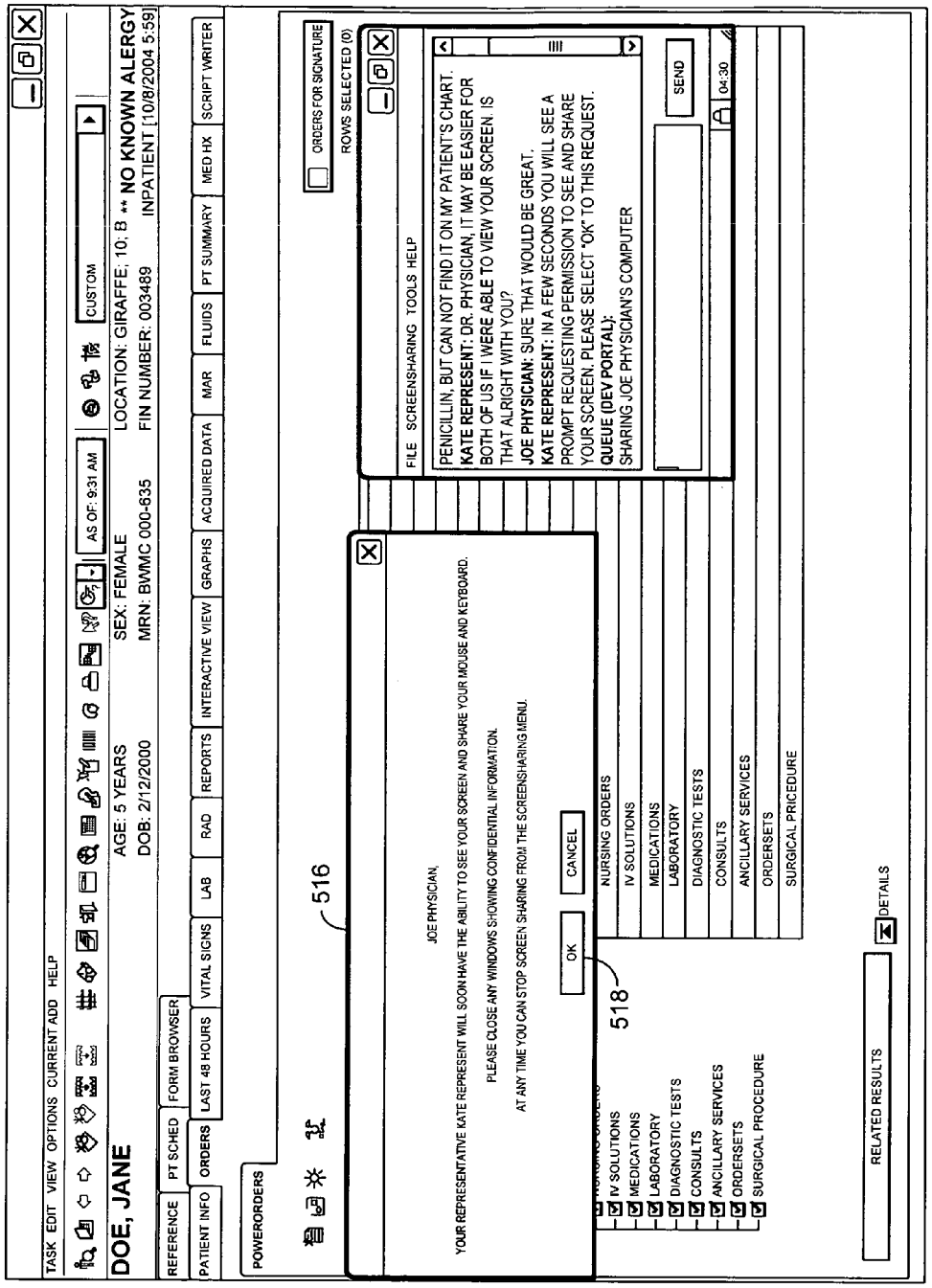

Turning now to FIG. 4, a flow diagram is illustrated showing an exemplary method 400 for initiating a technical support session between a client device, such as the client device 110 of FIG. 1, and a support device, such as one of the support devices 116, 118, 120 of FIG. 1, in accordance with an embodiment of the present invention. Initially, as shown at block 410, a command to initiate a technical support session is received at the client device. Typically, the command will be a user command indicating that an end user is requesting a technical support session. However, in some embodiments, the command to initiate a technical support session may be generated automatically, for example, if a predetermined condition within a clinical application on the client device or a predetermined condition on the client device itself occurs.

There are number of ways the client device may receive a user command to initiate a technical support session. By way of example only and not limitation, a clinical application (such as the clinical application 210 of FIG. 2) residing on the client device may include an icon within its toolbar that an end user may select if the end user wishes to initiate a technical support session. The clinical application may additionally or alternatively include a menu option, e.g., within its help menu, that an end user may select. If the clinical application does not support this functionality, an end user may be able to open a clinical support application (such as the clinical support application 212 of FIG. 2) residing on the client device to command the initiation of a technical support session. Further, an end user may open a web browser and access a clinical support application server (such as the clinical support application server 112 of FIG. 1) to begin the process.

After a command to initiate a technical support session is received, clinical context information is retrieved from the client device, as shown at block 412. For embodiments in which a thick clinical support application resides on the client device, the clinical context information is typically retrieved by the clinical support application. For embodiments in which a thin clinical support application resides on the client device or a web browser is used, the clinical support application server typically retrieves the clinical context information.

At block 414, a request to initiate a clinical session is sent to a queue manager (such as the queue manager 114 of FIG. 1). The request typically includes the clinical context information retrieved from the client device, although the request and clinical context information may be sent separately in some embodiments of the invention. The request may be sent from the client device if a thick clinical support application resides on the device. However, if a thin clinical support application or web browser is employed, the request may be sent from another component, such as the clinical support application server, for example.

After receiving the request, a support device is selected for the technical support session at block 416. Selection of a support device may be performed in a number of ways within the scope of the present invention. By way of example only and not limitation, in one embodiment, the queue manager simply selects the first available support device for the session. In another embodiment, the queue manager sends the session request to all available support devices. A support representative at one of the support devices may then accept the session request. In a further embodiment, the queue manager may select a support device based on the clinical context information included with the session request. For example, the queue manager may maintain profiles for support representatives and may associate each profile (either statically or dynamically) with a particular support device. Each profile may contain information regarding the capabilities of a support representative for assisting an end user. The queue manager may compare clinical context information (which may be included with a session request) with the various profiles to determine which support representative (and corresponding support device) would be most appropriate for assisting the end user who is requesting a technical support session. In yet a further embodiment, the queue manager may similarly identify multiple support representatives (and corresponding support devices) that are suitable for assisting an end user based on clinical context information and profiles and may forward the session request to each of those support devices. One of the support representatives may then accept the session request.

In some embodiments of the present invention, the queue manager or another component may also perform a security check, as shown at block 418. The purpose of the security check is to ensure that the support representative operating the selected support device is authorized to enter a technical support session and to assist the particular user. The security check may be performed, for example, by maintaining a database indicating authorizations for the various support representatives and accessing the database after a particular support device (and corresponding support representative) has been selected.

If the support representative for the selected support device is authorized to assist the end user, a technical support session is then initiated between the client device and the selected support device, as shown at block 420. In some embodiments, the technical support session may be initiated upon selection of a support device by the queue manager without further action at either the client device or the selected support device. In other embodiments, the technical support session may not be initiated until a support representative at a selected support device accepts a session request.

Once a technical support session has been initiated between the client device and a support device, the support representative may assist the end user in a wide variety of different ways. By way of example only and not limitation, the support representative and end user may use instant messaging for the session. The support representative and end user could alternatively carry on a telephone conference for the session. To aid the support representative in understanding the issue faced by the end user, the support device may receive and present clinical context information from the client device.

In some embodiments, the support representative may remotely view the display from the client device. In addition, the support representative may take remote control of the client device to assist the end user. To protect patient privacy and ensure HIPAA compliance in either remote viewing or control of the client device, the end user may be given proper notification, for example, to close any sensitive material. In addition, the end user must give permission via an approval window, for example, prior to a support representative remotely viewing or taking remote control of the client device.

If the support representative cannot fully assist the end user, the support representative may request other support representatives to join the session or hand the session off to other support representatives. The support representative may also determine that assistance from an entity other than a support representative is necessary. For example, the support representative may determine that the problem is a hardware issue with the client device and may contact a technician to physically inspect and/or repair the device.

Beyond providing technical assistance, the technical support session may also provide the ability for clinical assistance. For example, a clinician may be using a clinical application to manage medications for a patient. If the clinician has questions regarding certain medications for the patient, the clinician may wish to speak with a pharmacist. The clinician may initiate a session with a support representative, who may in turn contact or hand off the session to a pharmacist.

Either during the technical support session or after the session has ended, session information may be logged, as shown at block 422. Typically, session information will be logged at both an audit manager (such as the audit manager 214 of FIG. 2) for the client device and a client relations manager (such as the client relations manager 312 of FIG. 3) at the support device. However, in some embodiments of the invention, a single component may capture the session information.

Referring now to FIG. 5A through FIG. 5H and FIG. 6A through FIG. 6H, screen displays illustrating a technical support session in a clinical environment in accordance with an embodiment of the present invention are provided. Initially, FIG. 5A through FIG. 5H are screen displays showing the technical support session from the viewpoint of a client device (such as the client device 110 of FIG. 1). In this example, Dr. Joe Physician is having difficulty finding a prescription order that was placed for a patient, Jane Doe. The clinical application that Dr. Physician is using to manage care for Jane Doe is shown in the screen display 500A of FIG. 5A. In particular, the application is currently on the "Orders" tab 510, which may be used to show prescription orders. The application also includes a support session icon 512 that may be selected to initiate a technical support session.

After Dr. Physician selects the support session icon 512 (or otherwise initiates the support session), an instant messaging window 514 appears, as shown in the screen display 500B of FIG. 5B. Messages regarding the status of the session initiation process may be provided in the window 514. For example, when a support representative has arrived may be indicated. Here, the support representative is Kate Represent. Once the session has been initiated, Dr. Physician may type messages to and see messages from the support representative in the instant messaging window 514 as in a conventional instant messaging application.

Dr. Physician may explain the issue to the support representative, as shown in the screen display 500C of FIG. 5C. Here, Dr. Physician explains that he cannot find a penicillin order that was placed for the patient. As shown in the screen display 500D of FIG. 5D, the support representative may decide that the easiest way to resolve the issue would be to remotely view and control Dr. Physician's computer. The support representative asks whether this would be alright with Dr. Physician and explains that a prompt requesting permission will be presented on Dr. Physician's display.

The remote viewing/control prompt 516 presented on Dr. Physician's display is illustrated in the screen display shown 500E in FIG. 5E. As depicted, the prompt 516 explains that, if permission is given by Dr. Physician, the support representative will be able to see Dr. Physician's screen and control his mouse and keyboard. The prompt 516 also informs Dr. Physician to close any windows containing confidential information. In doing so, patient privacy and HIPAA requirements may be satisfied. To give remote viewing/control permission to the support representative, Dr. Physician may select the "OK" button 518 on the prompt 516.

Once the support representative has remote viewing/control capabilities, the support representative may navigate through the clinical application to assist Dr. Physician. As shown in the screen display 500F in FIG. 5F, the support representative opens a Filters window 520 to determine what filters are currently selected for the clinical application. By doing so, the support representative determines that the "Ordered" box 522 is not currently selected. After either the support representative or Dr. Physician selects the "Ordered" box 522, the penicillin order Dr. Physician was searching for is displayed under the "Orders" tab 510, as demonstrated on the screen display 500G of FIG. 5G. Having resolved Dr. Physician's issue, the support representative may determine if there are any other issues and, if not, may terminate the session. A session termination window 524 is then presented on Dr. Physician's display, as shown in the screen display 500H of FIG. 5H.

Figure 6A:
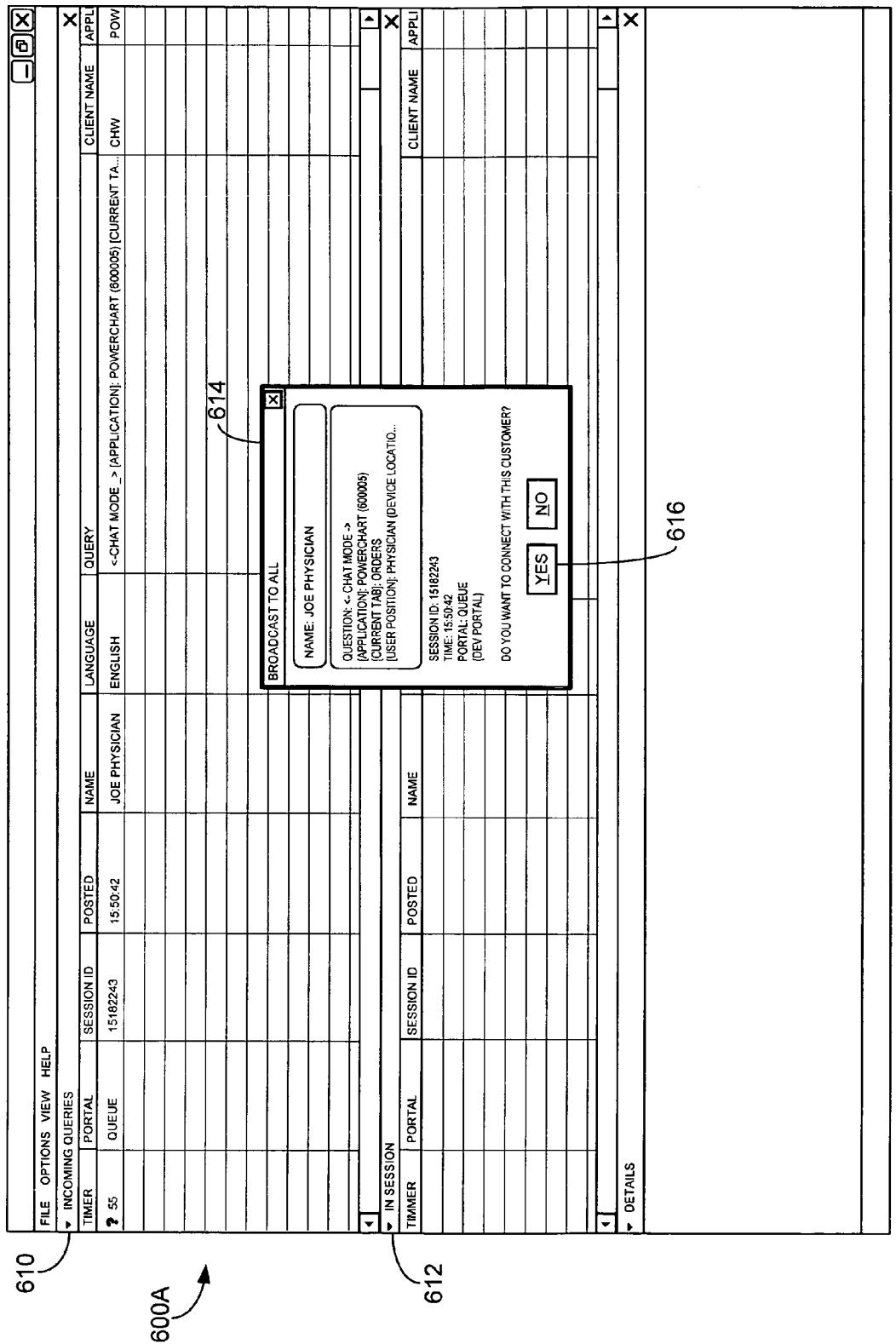
FIG. 6A through 6H are exemplary screen displays from a support device during a technical support session in a clinical environment in accordance with an embodiment of the present invention.

Referring now to FIG. 6A through FIG. 6H, screen displays are provided depicting the above-described technical support session from the viewpoint of the support device for the support representative. Initially, a display 600A for a technical support application is depicted in FIG. 6A. The display 600A includes an "Incoming Queries" portion 610, which provides information regarding support requests. For example, Dr. Physician's support request is shown on the first line of the incoming queries potion 610. The display 600A also includes an "In Session" portion 612, which provides information for any ongoing session. Here, the support representative is not currently engaged in a support session and no information is provided in the "In Session" portion 612. In addition to providing information for a support request in the "Incoming Queries" portion 610, a support request window 614 may be presented. The support request window 614 provides clinical context information to the support representative. For example, the support request window 614 indicates Joe Physician as the end user requesting support, the clinical application Dr. Physician is using (POWERCHART), and the current tab within the clinical application (ORDERS). It should be noted that the clinical context information provided in the support request window 614 is exemplary and other types of clinical context information may be provided.

Figure 6B:
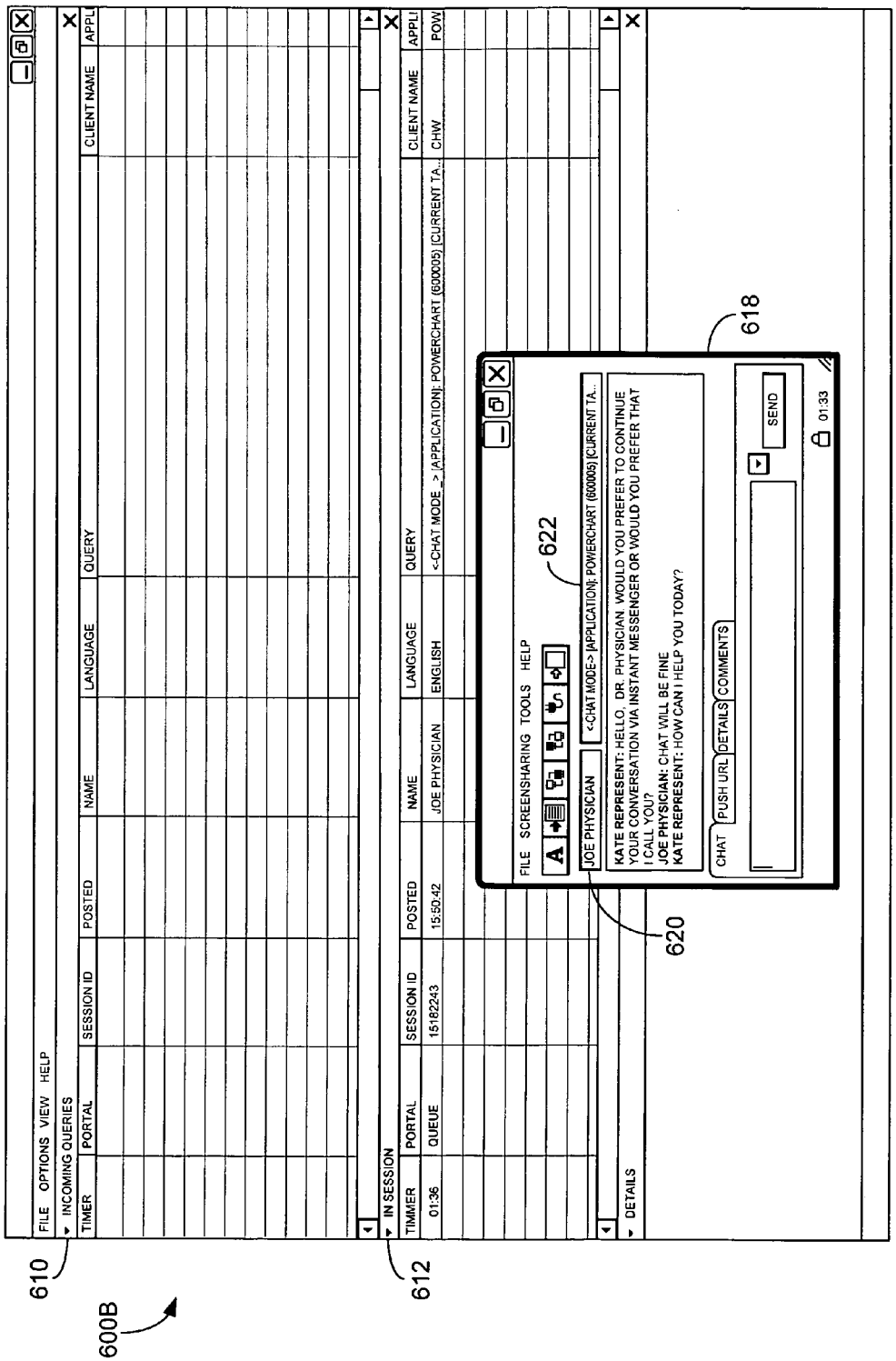

Once the support representative accepts the support session request (e.g., by selecting the "YES" button 616 from the support request window 614), an instant messaging window 618 is opened, as shown in the screen display 600B of FIG. 6B. In addition, information is removed from the "Incoming Queries" portion 610 and is now provided in the "In Session" portion 612 of the display, indicating that the support representative is currently in a support session. The instant messaging window 618 for the support representative also provides clinical context information within portions 620, 622 of the window 618.

Figure 6C:
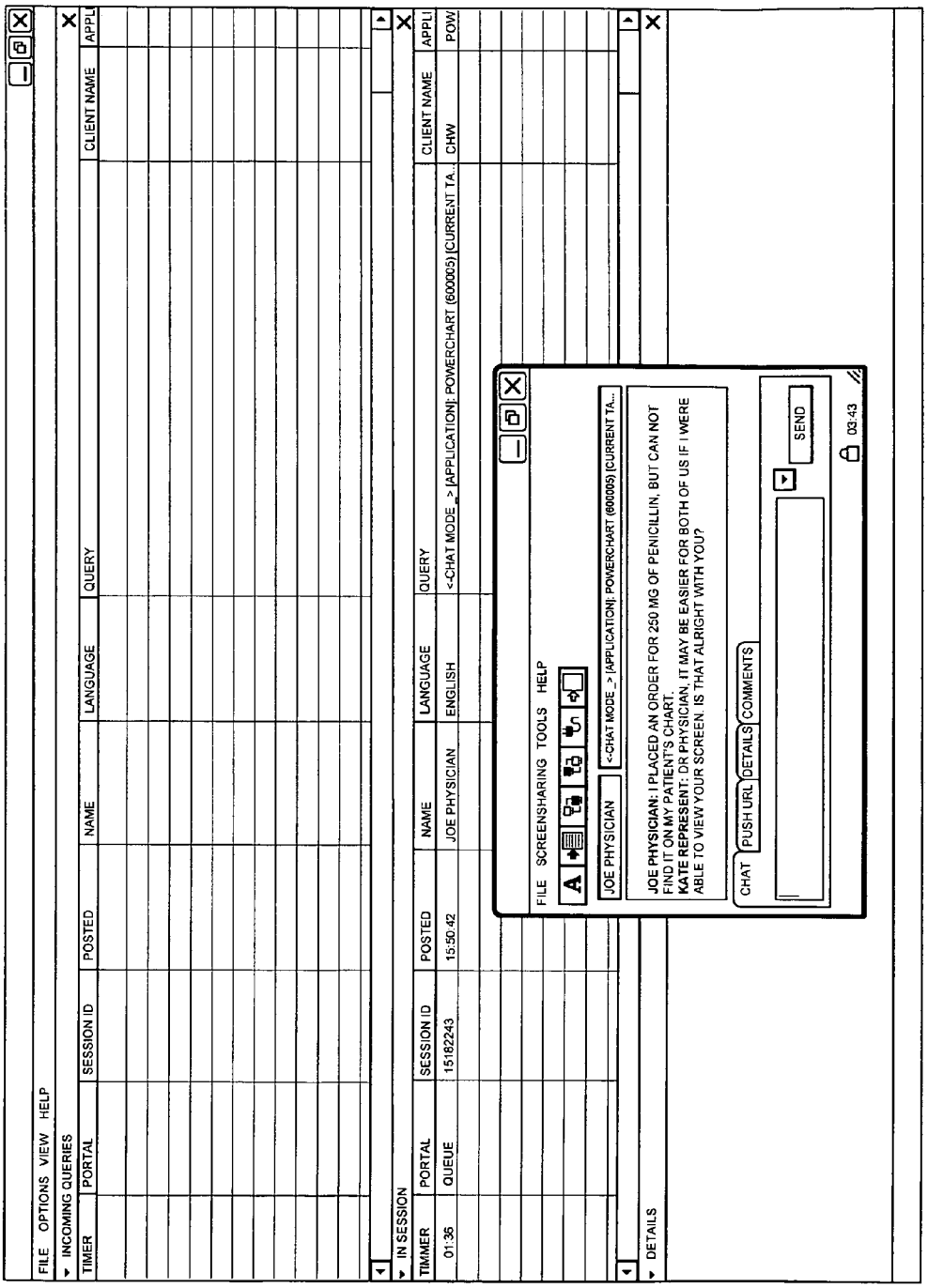
Figure 6D:
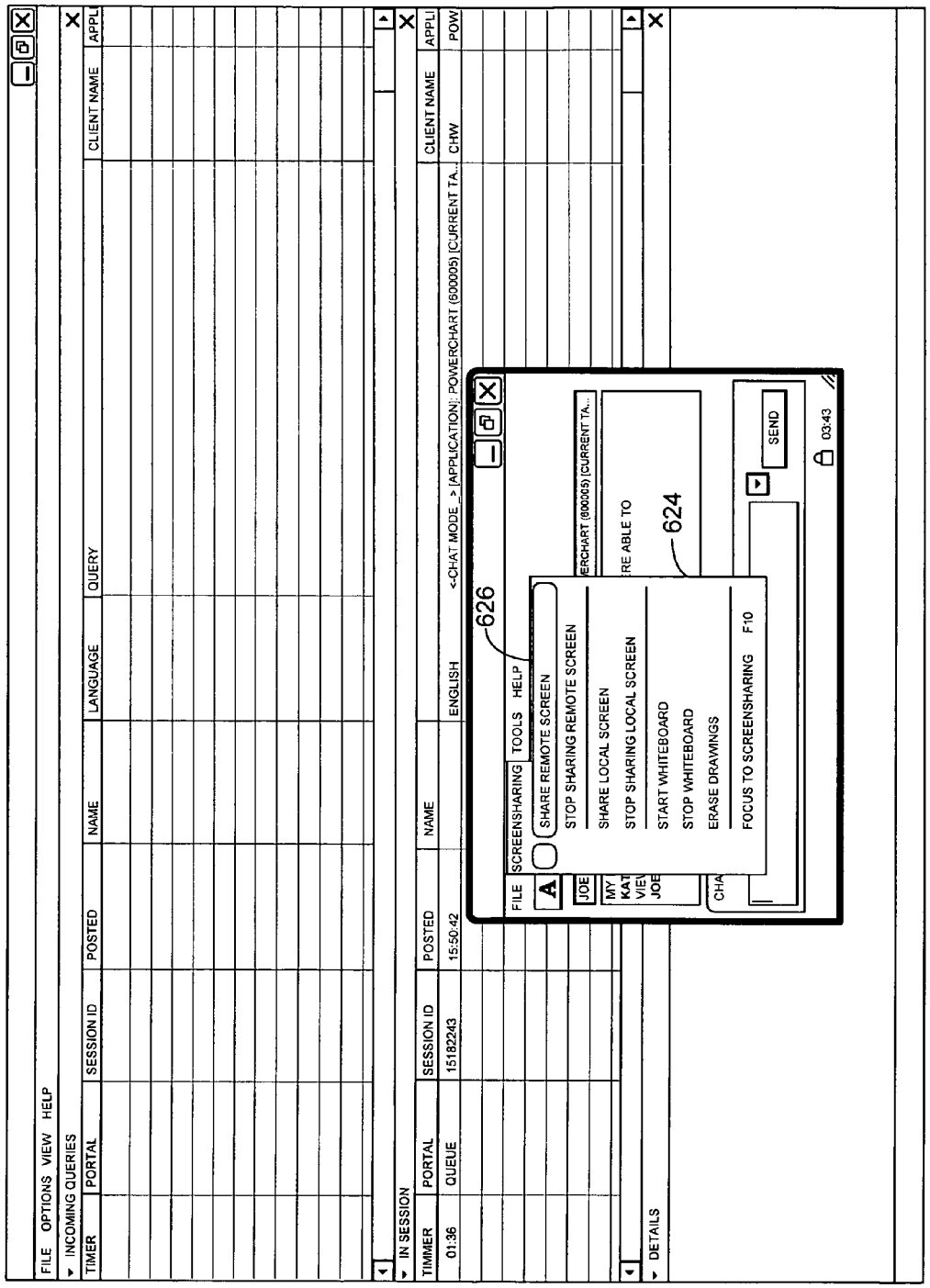
Figure 6E:
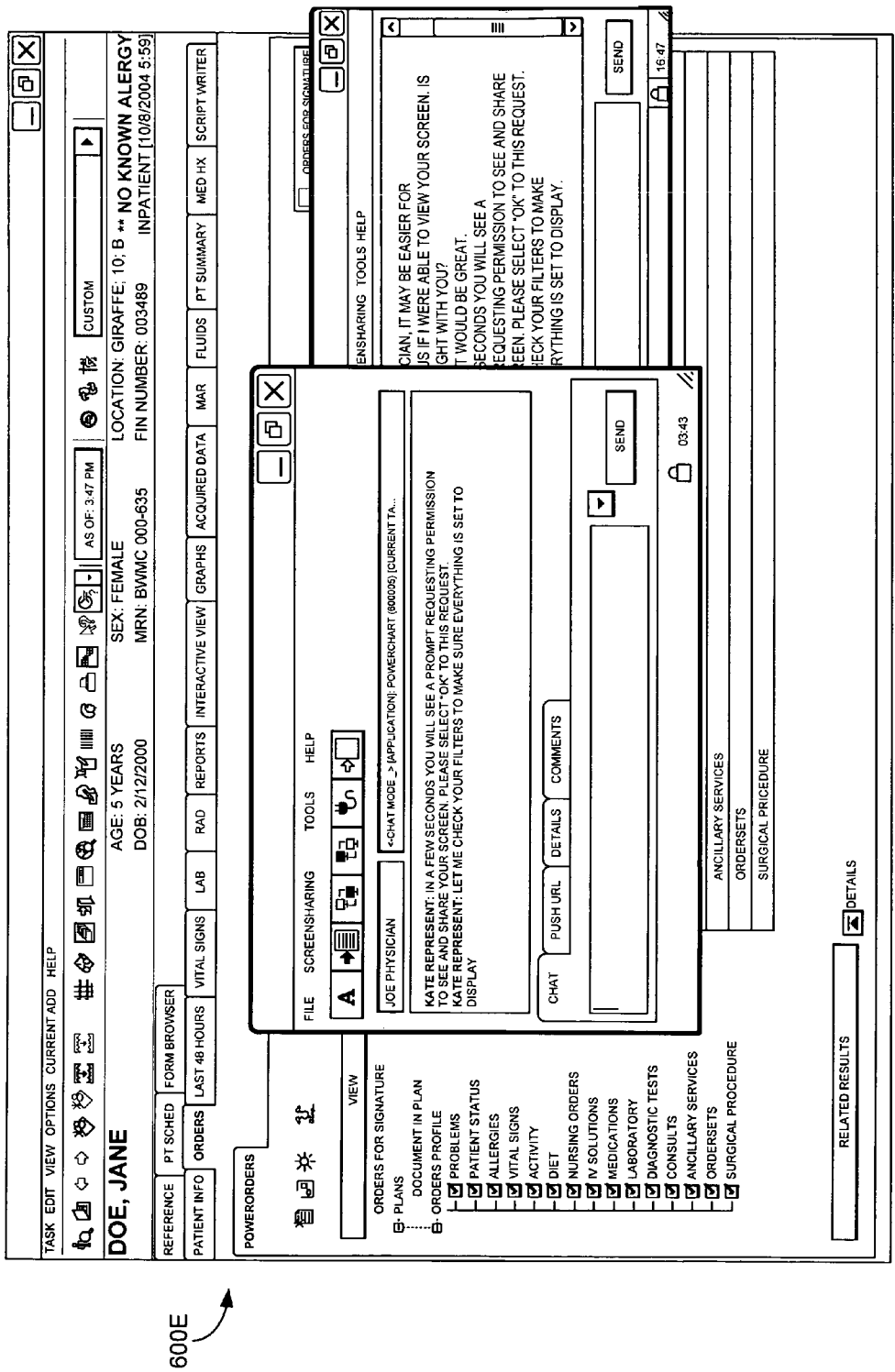
Figure 6F:
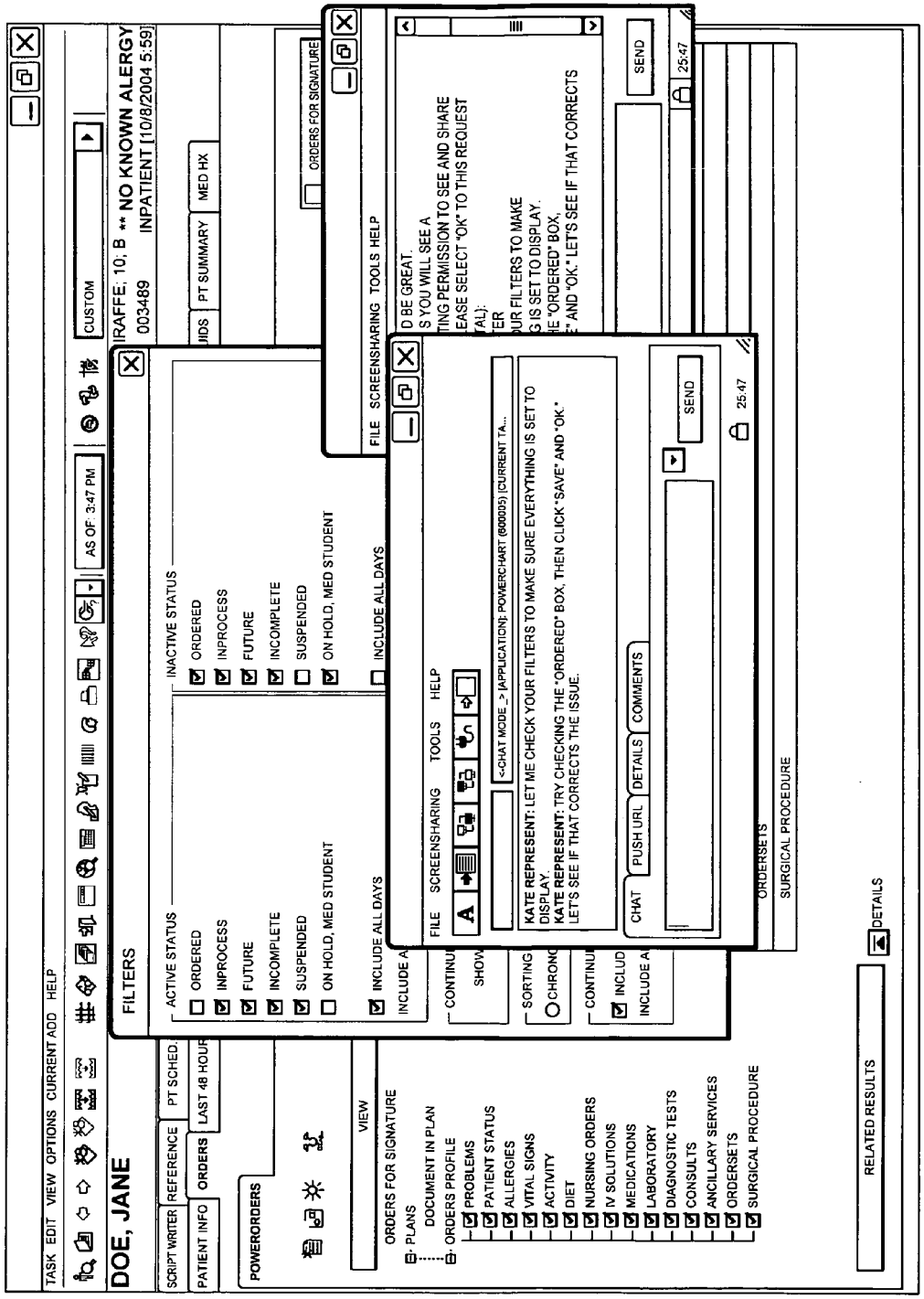

As discussed above and shown in the screen displays 600B and 600C of FIG. 6B FIG. 6C, respectively, Dr. Physician may describe the problem to the support representative, who may then determine that the easiest way to assist Dr. Physician is via remote viewing/control. The support representative may select a "ScreenSharing" drop down menu 624 and then may select the "Share Remote Screen" option 626, as shown in the screen display 600D of FIG. 6D. As discussed above, the selection does not automatically give the support representative remote viewing/control capability. Instead, a prompt is first provided to Dr. Physician, who then give permission via the prompt.

Figure 6G:
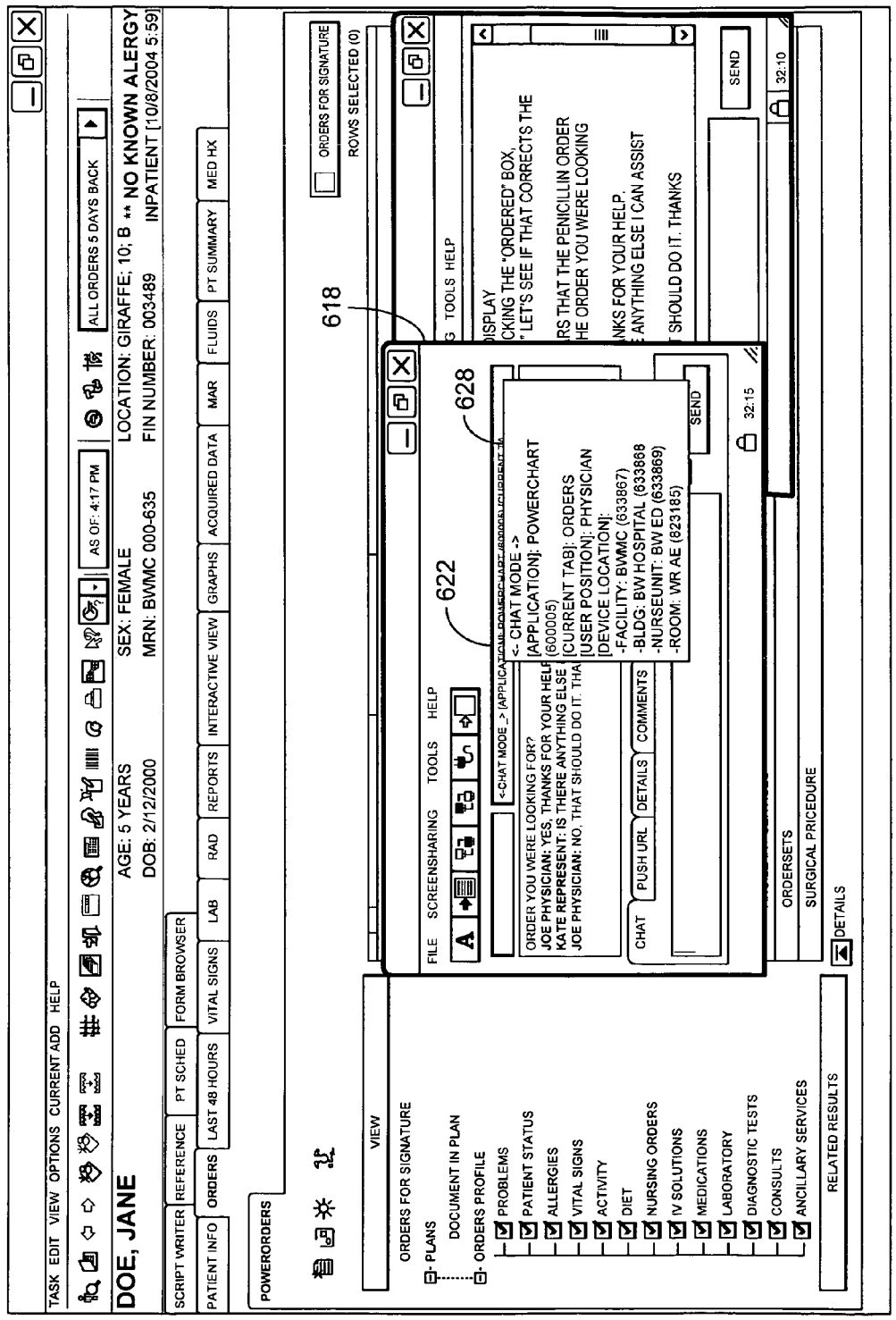
Figure 6H:
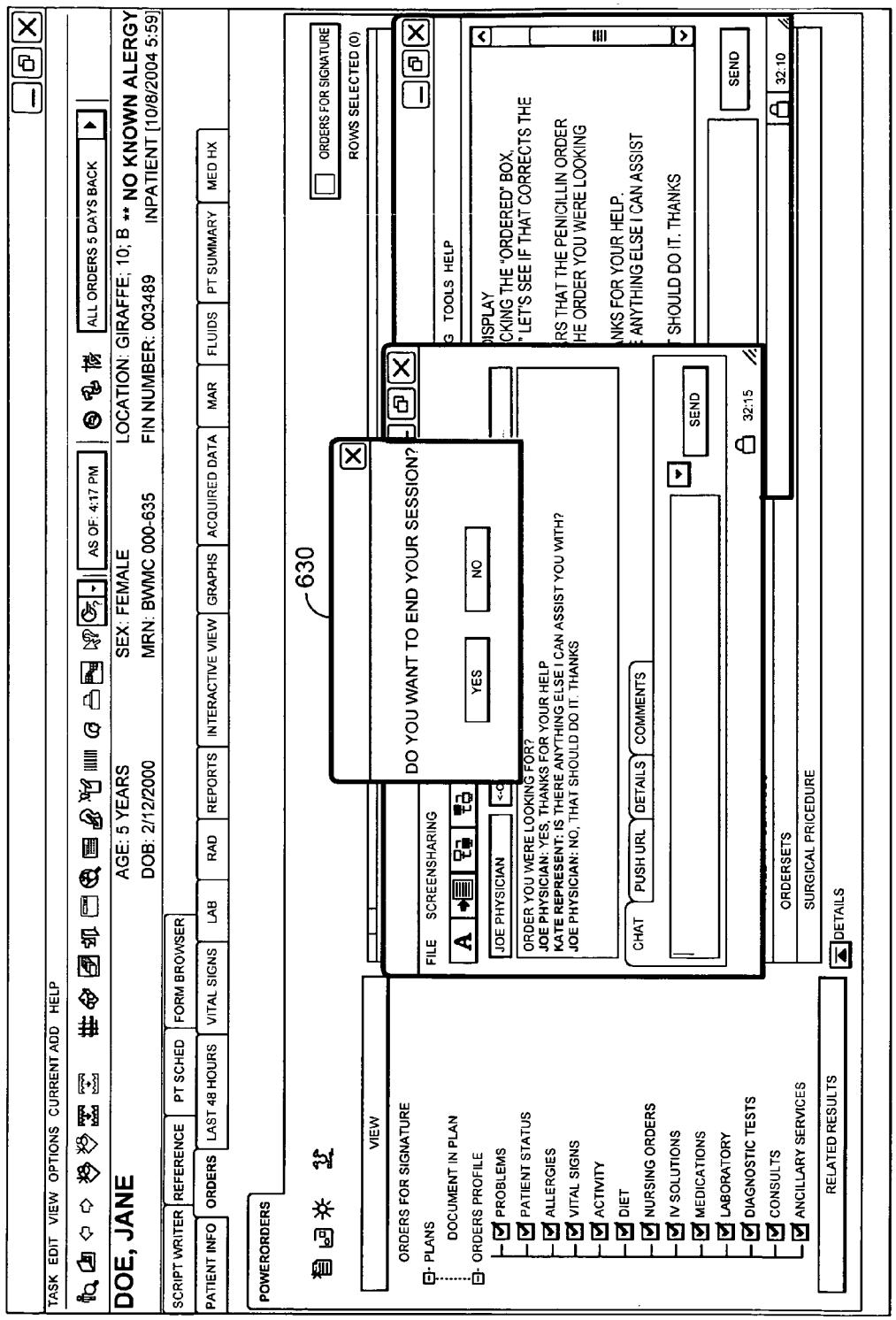

After Dr. Physician has given remote viewing/control permission, the support representative may view Dr. Physician's display as shown in the screen display 600E of FIG. 6E. In addition, the support representative may control Dr. Physician's computer to view the Filters window, as discussed above and as shown in the screen display 600F of FIG. 6F. It should be noted that at any time during the support session, the support representative may be able to view clinical context information for Dr. Physician's computer. For example, the screen display 600G of FIG. 6G depicts a clinical context information display 628 that may be presented upon selection of the portion 622 of the instant messaging window 618. The display 628 shows, for example, the clinical application (POWERCHART), the current tab within the clinical application (ORDERS), the user's role (PHYSICIAN), and the client device location (FACILITY, BLDG, NURSEUNIT, and ROOM). The clinical context information shown in the screen display 600G of FIG. 6G is exemplary and a plethora of other clinical context information may be presented within the scope of the present invention.

After assisting Dr. Physician, the support representative may end the session as shown in the screen display 600H of FIG. 6H. A session termination prompt 630 is presented to the support representative and may be selected to end the session.

The present invention has been described in relation to particular embodiments, which are intended in all respects to be illustrative rather than restrictive. Alternative embodiments will become apparent to those of ordinary skill in the art to which the present invention pertains without departing from its scope. Substitutions may be made and equivalents employed herein without departing from the scope of the invention as recited in the claims. For example, additional steps may be added and steps omitted without departing from the scope of the invention. It will be understood that certain features and subcombinations are of utility and may be employed without reference to other features and subcombinations. This is contemplated and within the scope of the claims.

The invention claimed is:

1. One or more non-transitory computer-storage media storing computer-useable instructions that, when used by a computing device, cause the computing device to perform a method in a clinical computing environment for initiating a technical support session between a client device and at least one support device, the method comprising:

receiving a request to initiate a technical support session including a technical support representative for a client device to aid a clinician employing a clinical application;

receiving clinical context information associated with the client device, wherein the clinical context information comprises data that aids the technical support representative in assisting the clinician during the technical support session;

automatically accessing a profile for each technical support representative and information about each of the at least one support device being operated by each technical support representative, wherein the profile of each technical support representative comprises capabilities of the technical support representative to assist the clinician who is requesting the technical support session;

determining the at least one skilled technical support representative for the technical support session based on matching the capabilities in the profile of each support representative, information about the associated support device being operated by each technical support representative, and the clinical context information associated with the client device;

accessing by the queue manager, a database maintained by the queue manager and containing the security authorization of each of the at least one skilled technical support representative, wherein the security authorization indicates whether each of the at least one skilled technical support representative is authorized to assist the clinician who is requesting the technical support session;

determining by the queue manager device, the at least one authorized technical support representative for the technical support session of the at least one skilled technical support representative based on the at least one skilled technical support representative's security authorization in the database to enter a technical support session and to assist the clinician who is requesting the technical support session;

determining by the queue manager device, the at least one support device for the technical support session being operated by the at least one authorized technical support representative for the technical support session; and initiating the technical support session between the client device and the at least one support device.

2. The one or more non-transitory computer-storage media of claim 1, further comprising providing the clinical context information to the at least one support device.

3. The one or more non-transitory computer-storage media of claim 1, wherein initiating a technical support session further comprises comparing the clinical context information associated with the client device with the information about the at least one support device.

4. The one or more non-transitory computer-storage media of claim 1, wherein the information about the at least one support device comprises a profile for each support representative operating the at least one support device.

5. The one or more non-transitory computer-storage media of claim 1, wherein the technical support session comprises a real-time session.

6. The one or more non-transitory computer-storage media of claim 1, wherein initiating a technical support session comprises:
communicating a session request to the at least one support device;
receiving a session acceptance from at least one of the at least one support device; and
initiating a technical support session between the client device and the at least one of the at least one support device.

7. The one or more non-transitory computer-storage media of claim 6, wherein communicating a session request to the at least one support device further comprises communicating clinical context information to the at least one support device.

8. A method in a clinical computing environment for providing technical support to a client device, the method comprising:
receiving by a queue manager device, clinical context information associated with a client device;
automatically accessing by the queue manager device, a profile for each technical support representative and information about each of the at least one support device being operated by each technical support representative, wherein the profile of each technical support representative comprises capabilities of the technical support representative to assist the clinician who is requesting the technical support session;
determining by the queue manager device, the skilled technical support representative for the technical support session based on matching the capabilities in the profile of each technical support representative, information about the at least one support device being operated by each technical support representative, and the clinical context information associated with the client device;
accessing by the queue manager, a database maintained by the queue manager and containing the security authorization of each of the at least one skilled technical support representative, wherein the security authorization indicates whether each of the at least one skilled technical support representative is authorized to enter a technical support session and assist the clinician who is requesting the technical support session;
determining by the queue manager device, the at least one authorized technical support representative for the technical support session of the at least one skilled technical support representative based on the at least one skilled technical support representative's security authorization in the database to enter a technical support session and to assist the clinician who is requesting the technical support session;
determining by the queue manager device, the at least one support device for the technical support session being operated by the at least one authorized technical support representative for the technical support session;
in response to determining the support device for the technical support session, communicating a session request to the at least one support device, wherein communicating a session request to the at least one support device further comprises communicating clinical context information to the at least one support device;
presenting the clinical context information on the at least one support device in one or more of an incoming queries area and a support request window before one of the at least one authorized technical support representative responds to the session request and the technical support session is initiated; and
moving the clinical context information from one or more of the incoming queries area and the support request window to an ongoing session area on the at least one support device after the at least one authorized technical support representative responds to the session request and the technical support session is initiated.

9. The method of claim 8, further comprising:
providing the technical support session between the client device and the at least one support device.

10. The method of claim 9, wherein the technical support session comprises a real-time session.

11. A method in a clinical computing environment for requesting a technical support session between a client device and at least one support device, the method comprising:
receiving from the client device a command from a clinician to automatically request the technical support session including a technical support representative to aid the clinician employing a clinical application;
directly upon receiving the command, automatically accessing clinical context information from the client device, wherein the clinical context information comprises data that aids the technical support representative in assisting the clinician during the technical support session including at least one of a characteristic of the client device, a characteristic of a clinical application, and information pertaining to the clinician;
communicating a request for the technical support session from the client device to a queue manager device;
communicating from the client device to the queue manager device, the clinical context information;
automatically accessing by the queue manager device, a profile for each technical support representative and information about each of the at least one support device being operated by each technical support representative, wherein the profile of each technical support representative comprises capabilities of the technical support representative to assist the clinician who is requesting the technical support session;
determining by the queue manager device, the at least one skilled technical support representative for the technical support session based on matching the capabilities in the profile of each technical support representative, information about the at least one support device being operated by each technical support representative, and the communicated clinical context information from the client device;
accessing by the queue manager, a database maintained by the queue manager and containing the security authorization of each of the at least one skilled technical support representative, wherein the security authorization indicates whether each of the at least one skilled technical support representative is authorized to enter a technical support session and assist the clinician who is requesting the technical support session;

determining by the queue manager device, the at least one authorized technical support representative for the technical support session of the at least one skilled technical support representative based on the at least one skilled technical support representative's security authorization in the database to enter a technical support session and to assist the clinician who is requesting the technical support session;

determining by the queue manager device, the at least one support device for the technical support session being operated by the at least one authorized technical support representative for the technical support session;

initiating the technical support session between the client device and the at least one support device in response to determining the at least one support device for the technical support session; and communicating the clinical context information to the at least one support device in response to the initiation of the technical support session.

12. The method of claim 11, wherein the technical support session comprises a real-time session.

13. The method of claim 11, wherein the clinical context information comprises at least one of an end user's identification, an end user's location, an end user's role, an identification of a clinical application, a name of a clinical application, a current tab within a clinical application, a current location within a clinical application, a physical location of the client device, a software characteristic of the client device, and a hardware characteristic of the client device.

* * * * *